United States Patent [19]

Hayashi et al.

[11] Patent Number: 5,038,030
[45] Date of Patent: Aug. 6, 1991

[54] SURFACE IDENTIFICATION FOR BACK-COATED MAGNETIC RECORDING MEDIUM

[75] Inventors: Youichi Hayashi; Kazuo Kubota; Masaaki Sakaguchi, all of Kanagawa, Japan

[73] Assignee: Fuji Photo Film Co., Ltd., Kanagawa, Japan

[21] Appl. No.: 360,637

[22] Filed: Jun. 2, 1989

[30] Foreign Application Priority Data

Jun. 3, 1988 [JP] Japan .................... 63-136891

[51] Int. Cl.$^5$ ................................ G02F 1/01
[52] U.S. Cl. .......................... 250/225; 356/366
[58] Field of Search ........ 250/225; 356/366, 367–369; 242/57; 365/122

[56] References Cited

U.S. PATENT DOCUMENTS 4,410,277  10/1983  Yamamoto et al. ............. 356/366

Primary Examiner—David C. Nelms
Assistant Examiner—S. Allen
Attorney, Agent, or Firm—Sughrue, Mion, Zinn Macpeak & Seas

[57] ABSTRACT

When a light beam is applied to a surface of a back-coated magnetic recording medium such as a long magnetic tape, the light reflected by the recording medium surface is polarized. The angle of rotation of the plane of polarization of light reflected by the magnetic layer of the recording medium is different from the angle of rotation of the plane of polarization of light reflected by the back coating layer of the recording medium. The light reflected from the surface of the recording medium is applied to a polarizer which allows only linearly polarized light that vibrates in a predetermined direction to pass through itself. Then, the intensity level of the linearly polarized light is detected to determine whether the light was reflected from the magnetic layer or the back coating layer.

6 Claims, 3 Drawing Sheets

SURFACE IDENTIFICATION FOR BACK-COATED MAGNETIC RECORDING MEDIUM

BACKGROUND OF THE INVENTION

1. Field of the Invention

The present invention relates to a method and an apparatus for identifying a surface of a long back-coated magnetic recording medium such as a magnetic tape to determine whether the magnetic recording medium is being properly wound around a hub or the like without being reversed or turned wrong side out as it is continuously supplied to the hub or the like.

2. Description of the Prior Art

There is known a high-density recording magnetic tape having a magnetic layer coated on one side and a back coating layer such as a carbon layer coated on the other side. Such magnetic tape, which is used for high-density recording, is manufactured in the same manner as ordinary magnetic tape. A continuous blank magnetic tape, which is about 2 to 50 times longer than commercially available magnetic tapes, is wound around a blank tape hub, and subsequently unreeled and cut to a certain length depending on the use to which it will be put. The unwound magnetic tape is wound again around a product hub before it is sold.

High-density recording magnetic tape is very thin, about 3 to 50 μm thick, and hence flexible, and is also narrow, about 3 to 51 mm wide. When high-density recording magnetic tape is subjected to tension fluctuations or tortuous motions while it is being transported, the tape tends to become easily reversed or turned wrong side out. It may be wound around a product hub properly for part of its length, and then somewhere along its length become turned so that the wrong side faces out. Tension fluctuations or tortuous motions may not be strong enough to reverse a magnetic tape somewhere along its length as the tape is being wound around a product hub. However, if a blank magnetic tape is erroneously wound around a tape blank hub with the wrong side out over its entire length, then a length of tape cut from the blank tape will also be wound around a product hub with the wrong side out over the entire length thereof.

In order to prevent a magnetic tape which is wound around a product hub and has become reversed over part or all of its length from being shipped and offered for sale, as the tape is being wound around the product hub, it is necessary to inspect whether the magnetic tape is being properly wound around the product hub or has become reversed. A simple device for inspecting a tape surface applies light to the tape surface while the tape is being transported at a high speed and measures the difference between the intensity of the applied light and the intensity of the light reflected from the tape surface. Such an inspecting device is advantageous since with it the entire tape surface can be inspected quickly and simply. However, the device cannot perform stable inspection because the ratio of the intensity of the light reflected from the front of the tape to that reflected from the back of the tape is small, i.e., about 1.5, and also because the tape vibrates up and down as it is transported.

One conventional tape surface identifying device has a first detecting means which is operable when the tape is not moving and determines whether a surface (e.g., an outer surface) of a tape at each of the starting and terminal ends of the tape is the front or back of the tape, and a second detecting means which is operable when the tape is moving and continuously measures the width of the tape to check if the tape has become reversed (see Japanese Unexamined Utility Model Publication No. 57(1982)-138048). If the result of the detection carried out by either one of the first and second detecting means indicates an undesirable condition, then the tape is regarded as a defective tape.

The earlier device is disadvantageous for various reasons. Since it has two detecting means, it is large in size, costly to manufacture, and requires a complex maintenance procedure. The second detecting means cannot detect a tape reversal which occurs at a position outside its detecting range. Inasmuch as the ratio of the intensity of the light reflected from the magnetic layer to that reflected from the back coating layer of a back-coated magnetic tape is not large, it is difficult to effect accurate surface identification even when the tape is at rest. A detector which detects the intensity of the reflected light and is employed as the first detecting means, therefore, often fails to identify a tape surface properly.

SUMMARY OF THE INVENTION

It is an object of the present invention to provide a method and device for identifying a surface of a magnetic recording medium such as a magnetic tape with high accuracy to determine whether the magnetic recording medium has become reversed while it is being transported, or wound around a hub in a reversed condition over its entire length, the device being small in size, inexpensive to manufacture, and requiring simple maintenance.

According to the present invention, there is provided a method for identifying a surface of a back-coated magnetic recording medium composed of a base, a magnetic substance on one surface of the base, and another substance on the opposite surface of the base, the other substance having an optical anisotropy which is different from the optical anisotropy of the magnetic substance, the method comprising the steps of applying an optical beam to a surface of the recording medium, causing light reflected by the surface of the recording medium to impinge upon a polarizer, which allows only linearly polarized light vibrating in a predetermined direction to pass therethrough, and identifying the surface on the basis of the intensity of the linearly polarized light which has passed through the polarizer.

According to the present invention, there is also provided an apparatus for identifying a surface of a back-coated magnetic recording medium composed of a base, a magnetic substance on one surface of the base, and another substance on the opposite surface of the base, the other substance having an optical anisotropy which is different from the optical anisotropy of the magnetic substance, the apparatus comprising means for applying an optical beam to a surface of the recording medium, polarizing means which pass therethrough only linearly polarized light in the light reflected by the surface of the recording medium, the linearly polarized light vibrating in a predetermined direction, light detecting means for detecting the linearly polarized light that has passed through the polarizing means and generating an electric signal commensurate with the intensity of the linearly polarized light, and identifying means connected to the light detecting means for comparing the level of the electric signal with a reference level to identify the surface of the recording medium.

When a light beam is applied to a surface of a back-coated magnetic recording medium, the light reflected by the recording medium surface is polarized light. The angle of rotation of the plane of polarization of the light reflected by the magnetic layer of the recording medium is different from the angle of rotation of the plane of polarization of the light reflected by the back coating layer of the recording medium.

A coating, evaporation, sputtering or other process may be used to deposit the magnetic and back coating layers on the base of the recording medium.

The light beams reflected by the magnetic and back coating layers of the recording medium are polarized, and the angles of rotation of the planes of polarization of these reflected light beams are different from each other, as described above. The light reflected from the surface of the recording medium is applied to the polarizing means which allows only linearly polarized light that vibrates in a predetermined direction to pass therethrough. Then, the intensity level of the linearly polarized light is detected to determine whether the light was reflected from the magnetic layer or the back coating layer.

The light beam applied to the surface of the magnetic recording medium should preferably be of polarized light so that an increase in the ratio of the intensity of the linearly polarized light reflected by the magnetic layer to that reflected by the back coating layer can be effected by adjusting the angle of rotation of the polarizing means.

The above and other objects, features and advantages of the present invention will become more apparent from the following description when taken in conjunction with the accompanying drawings in which preferred embodiments of the present invention are shown by way of illustrative example.

DESCRIPTION OF THE PREFERRED EMBODIMENT

Figure 1:
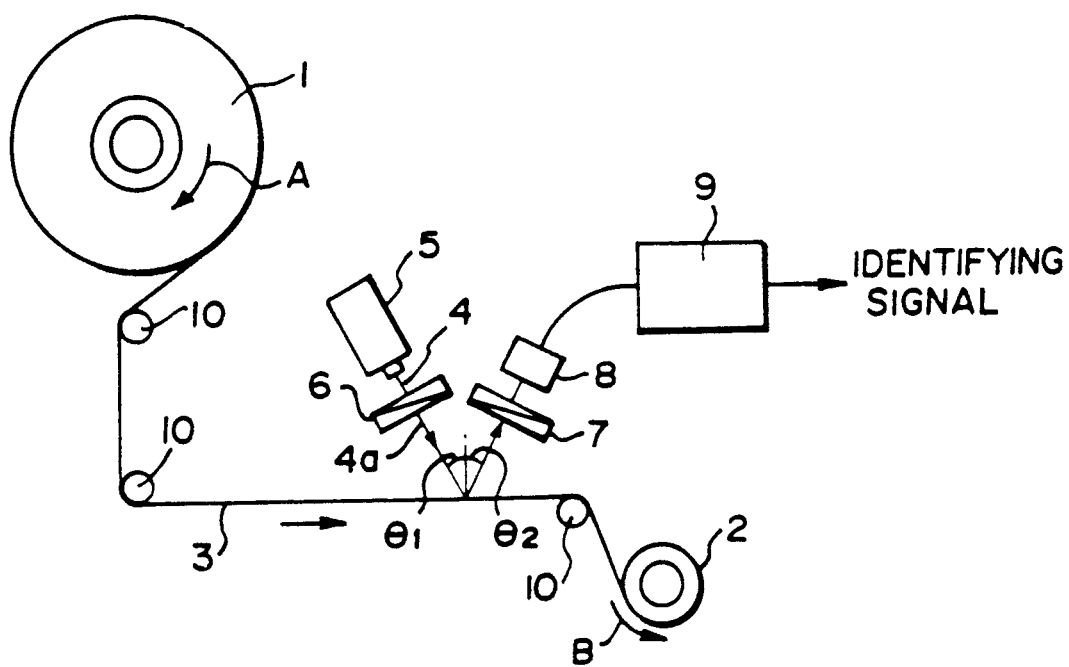
FIG. 1 is a schematic view of a surface identifying device according to the present invention.

FIG. 1 shows a surface identifying device according to the present invention being used in a tape winding process. The surface identifying device includes a magnetic tape transport means (not shown) for rotating a tape blank hub 1 about its own axis in the direction indicated by the arrow A and a product hub 2 about its own axis in the direction indicated by the arrow B, which transports a back-coated magnetic tape 3 for video use at a high speed from the tape blank hub 1 to the product hub 2. The surface identifying device also comprises a light beam applying means 5 which applies a light beam 4 to a surface of the magnetic tape 3 which is being transported, a polarizing plate 6 disposed between the light beam applying means 5 and the surface of the magnetic tape 3 which allows only P-polarized light 4a in the light beam 4 which has its plane of vibration aligned with the plane of incidence on the polarizing plate 6 to pass through itself, a polarizing plate 7 for blocking P-polarized light in the light reflected from the surface of the magnetic tape 3, the polarizing plate 7 being positioned such that its principal plane (containing the light incident thereon and the crystal optical axis) and the principal plane of the polarizing plate 6 extend perpendicularly to each other, a light detecting means 8 for detecting the light that has passed through the polarizing plate 7 and producing an electric signal corresponding to the intensity of the detected light, and an identifying means 9 for comparing the level of the electric signalproduced by the light detecting means 8 with a reference level and producing a signal representing the result of the comparison. Guide rollers 10 are disposed between the hubs 1, 2 for guiding the tape 3 and changing its direction of travel.

The back-coated magnetic tape 3 comprises a long transparent base of plastics, a magnetic layer 11 (FIG. 2) on one surface of the base, and a back coating layer 12 on the other surface of the base. The magnetic layer is made up mainly of Fe and vinyl chloride, for example, whereas the back coating layer is made up mainly of carbon and nitrocellulose, for example. Each of the magnetic layer and the back coating layer has an optical anisotropy such that it polarizes a light beam when it reflects the light beam. The magnetic and back coating layers, however, have different magnitudes of optical anisotropy, so that the angles of rotation of the planes of polarization of polarized lights reflected from these layers are different from each other. It is considered that the different magnitudes of optical anisotropy result from different refractive indexes n and different coefficients of light absorption k of these layers. For example, the magnetic layer has a refractive index n of 1.88 and a light absorption coefficient k of 0.81, whereas the back coating layer has a smaller refractive index n of 1.29 and a smaller light absorption coefficient k of 0.45. According to the surface identifying device of the present invention, the magnetic and back coating layers can be differentiated from each other if the difference between the refractive indexes n of these layers is 0.2 or greater.

The magnetic tape transport means may be of any construction insofar as it can transport the magnetic tape 3 while keeping a constant tension on it. The light beam applying means 5 may comprise a white-light lamp, a halogen lamp, or a red-light LED, for example. Each of the polarizing plates 6, 7 may comprise a sheet-like dichroic polarizing plate. The light detecting means 8 may comprise a gallium-arsenide photodiode, for example.

The angle $\theta_1$ of incidence of the P-polarized light 4a on the magnetic tape 3 and the angle $\theta_2$ of reflection of the P-polarized light 4a from the magnetic tape 3 are equal to each other and therefore allow the light detecting means 8 to detect light of regular reflection. Preferably, these angles $\theta_1$, $\theta_2$ are selected to be close to the Brewster angle $\theta_B$, at which the P-polarized light is reflected the least by the exposed surface of the base of the magnetic tape 3. If the refractive index of air is 1.0 and the refractive index of the base is 1.5, then the Brewster angle $\theta_B$ is about 56°. The P-polarized light 4a should preferably be applied to the magnetic tape 3 in the vicinity of the nearby guide roller 10 because the magnetic tape 3 is subjected to less vibration, deformation, curl, and the like near the guide roller 10.

The identifying means 9 may comprise a comparator for comparing a voltage signal having a level commensurate with the intensity of light detected by the light detecting means 8 with a reference voltage. If the level of the voltage signal is higher than the level of the reference voltage, then the identifying means 9 produces a high-level signal. If the level of the voltage signal is lower than the level of the reference voltage, then the identifying means 9 generates a low-level signal. The output signal from the light detecting means 8 and the output signal from the identifying means 9 may be either analog or digital signals. The input/output units of the identifying means 9 are selected so that they can receive and issue such analog or digital signals. The identifying signal from the identifying means 9 may be sent to a display means such as an LED to allow an operator to confirm the result visually, or may be applied to the control circuit of an automatic sorting means which determines whether the inspected magnetic tape 3 is acceptable or defective depending on the identifying signal and puts it with an appropriate group of tapes.

Figure 2:
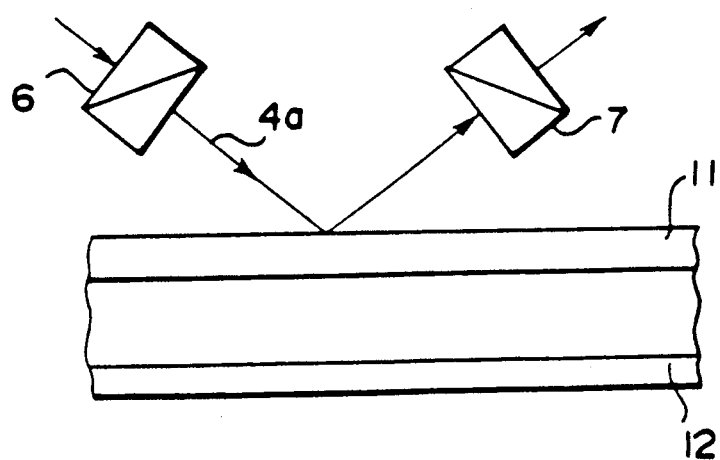
FIG. 2 is an enlarged fragmentary view of a polarizer and an analyzer of the device shown in FIG. 1.

The manner in which the P-polarized light 4a is reflected by the magnetic tape 3 will be described below with reference to FIG. 2. In FIG. 2, the polarizing plate 6 is referred to as a polarizer and the polarizing plate 7 is referred to as an analyzer.

When the P-polarized light 4a is radiated onto the magnetic layer 11, the P-polarized light 4a is reflected by the exposed surface of the magnetic layer 11. The polarized light which is reflected by the magnetic layer 11 has its plane of polarization rotated through a large angle, is elliptically polarized light and has P- and S-polarized components.

If the magnetic tape 3 has become reversed or the wrong side of it is turned out, the P-polarized light 4a will be applied to the carbon (back coating) layer 12. Then the plane of polarization of the polarized light which is reflected by the carbon layer 12 is not substantially rotated, and the reflected polarized light is elliptically polarized and close to P-polarized light. Since the analyzer 7 is positioned such that the principal plane thereof and the principal plane of the polarizer 6 extend perpendicular to each other, i.e., P-polarized light does not pass through the analyzer 7, almost no light reflected by the carbon layer 12 passes through the analyzer 7. However, since the S-polarized component of the light reflected by the magnetic layer 11 has a certain intensity, the intensity of the light beam which passes through the analyzer 7 has a certain magnitude. Therefore, the level of the intensity of the light detected by the light detecting means 8 when P-polarized light 4a is applied to the magnetic layer 11 is widely different from the level of the intensity of the light detected by the light detecting means 8 when P-polarized light 4a is applied to the carbon layer 12.

Figure 3:
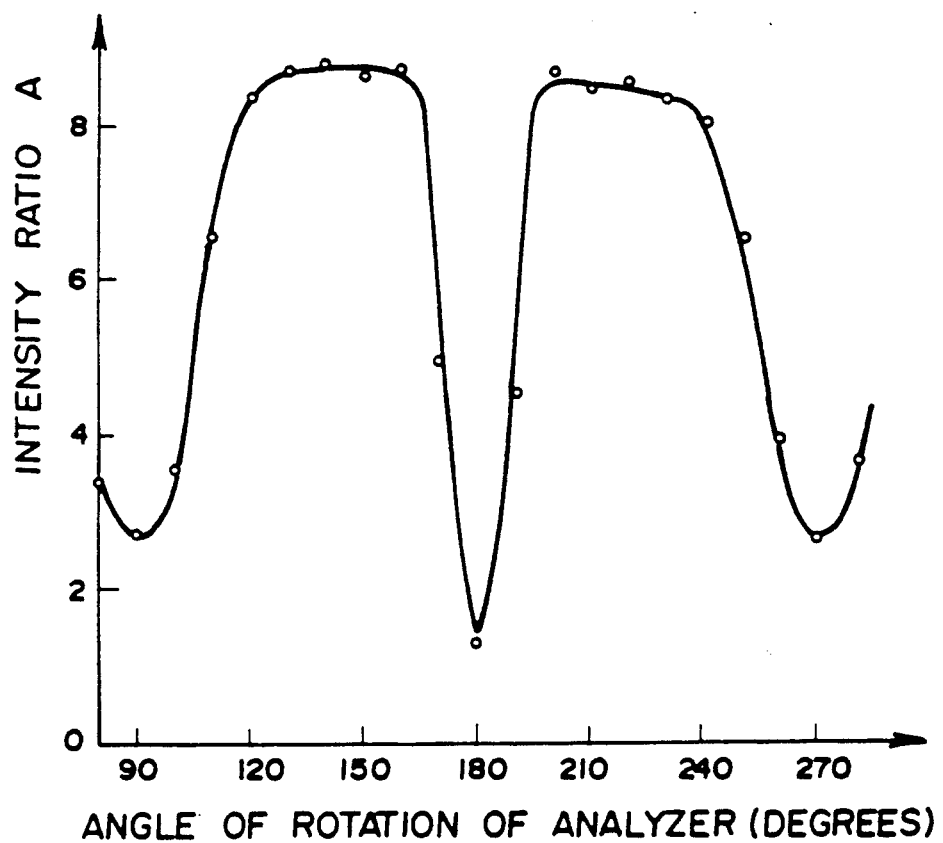
FIGS. 3 and 4 are graphs showing how the ratio of outputs from a light beam detecting means varies as the analyzer rotates.

The ratio A of the intensity of the light detected when the magnetic layer 11 is irradiated with P-polarized light 4a to the intensity of the light detected when the carbon layer 12 is irradiated with P-polarized light 4a varies according to the angle of rotation of the analyzer 7 about the light beam applied thereto. FIG. 3 shows how the ratio A varies with the angle of rotation of the analyzer 7. The angle of rotation of the analyzer 7 when the ratio A was the smallest was 180°. The angle of the polarizer 6 was finely adjusted to maximize the ratio A each time the reflected light was detected. The angle $\theta_1$ of incidence is set to 55° which is close to the Brewster angle. As illustrated in FIG. 3, the ratio A can be increased if the angle of rotation of the analyzer 7 is adjusted, and an intensity ratio can be obtained which is much higher than a ratio of 3, which is the smallest ratio with which a tape surface can reliably be identified.

Figure 4:
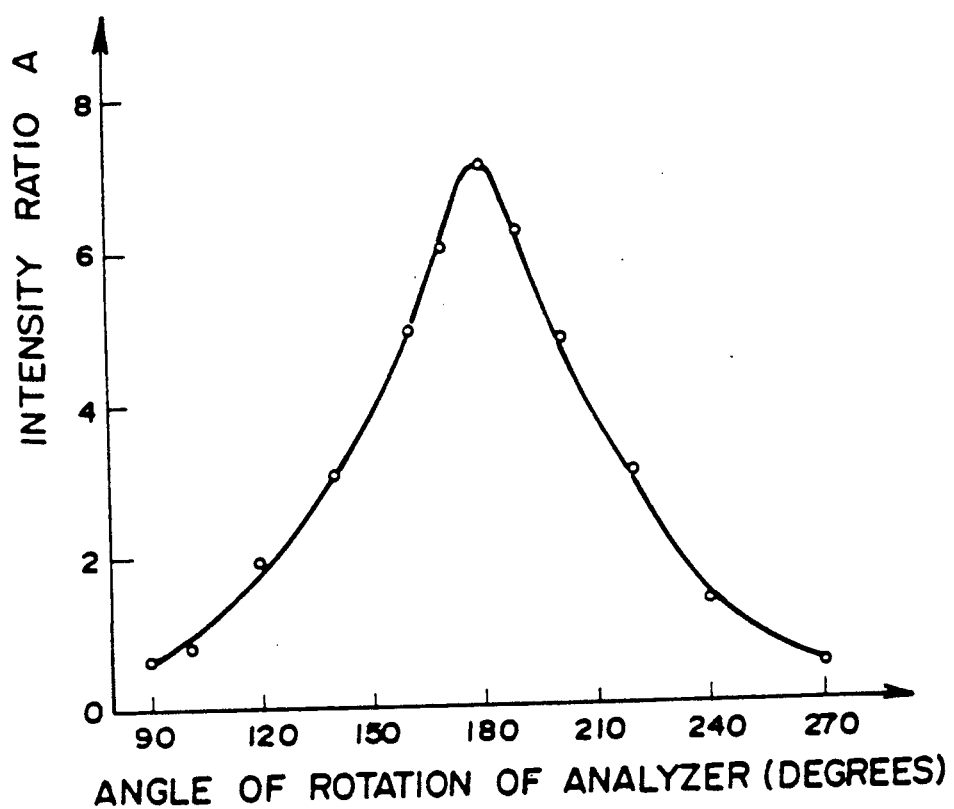

While the polarizer 6 is included in the above embodiment, it may be dispensed with since the magnetic layer 11 and the carbon layer 12 act as polarizers. FIG. 4 shows the results of an experiment conducted on a surface identifying device in the same manner as the experiment shown in FIG. 3, except that no polarizer 6 was used. As shown in FIG. 4, the angle range in which a desirable intensity ratio can be obtained is smaller than that which can be obtained with a surface identifying device having the polarizer 6. In the experiment of FIG. 4, the angle of rotation of the analyzer which maximized the intensity ratio A was 180°.

The surface identifying device of the present invention can inspect not only magnetic tape but also other types of tape such as abrasive tape. The light beam applying means and the light detecting means are not limited to those described above, but may be of any of various other types. The light detecting means is not limited to a specific detector, but may be a human eye. The principles of the present invention are not limited to the identification of a surface of a long tape but may be applied to the identification of a surface of a wide sheet or the like.

Although a certain preferred embodiment has been shown and described, it should be understood that many changes and modifications may be made therein without departing from the scope of the appended claims.

We claim:

1. A method for identifying a surface of a back-coated magnetic recording medium composed of a base, a magnetic substance on one surface of the base, and another substance on the opposite surface of the base, the other substance having an optical anisotropy which is different from the optical anisotropy of the magnetic substance, said method comprising the steps of:
   applying an optical beam to a surface of the recording medium;
   causing light reflected by said surface of the recording medium to impinge upon a polarizer, which allows only linearly polarized light in the reflected light, which linearly polarized light vibrates in a predetermined direction, to pass therethrough; and
   identifying said surface on the basis of the intensity of the linearly polarized light which has passed through said polarizer, to thereby determine whether said magnetic substance or said other substance is facing said optical beam.

2. The method for identifying a surface of a back-coated magnetic recording medium according to claim 1, further comprising the step of passing the optical beam through a polarizing plate before the optical beam reaches said surface of the recording medium, said polarizing plate allowing only P-polarized light of the optical beam to pass therethrough.

3. The method for identifying a surface of a back-coated magnetic recording medium according to claim 1, wherein the recording medium comprises an elongate magnetic tape.

4. An apparatus for identifying a surface of a back-coated magnetic recording medium composed of a base, a magnetic substance on one surface of the base, and another substance on the opposite surface of the base, the other substance having an optical anisotropy which is different from the optical anisotropy of the magnetic substance, said apparatus comprising:

means for applying an optical beam to a surface of the recording medium;

polarizing means which pass therethrough only linearly polarized light in the light reflected by said surface of the recording medium, the linearly polarized light vibrating in a predetermined direction;

light detecting means for detecting the linearly polarized light that has passed through said polarizing means and generating an electric signal commensurate with the intensity of the linearly polarized light; and identifying means connected to said light detecting means for comparing the level of said electric signal with a reference level to identify said surface of the recording medium, to thereby determine whether said magnetic substance or said other substance is facing said optical beam.

5. The apparatus according to claim 4, further comprising a polarizing plate disposed between said means for applying an optical beam and said surface of the recording medium, said polarizing plate allowing only P-polarized light of the optical beam to pass therethrough.

6. The apparatus according to claim 4, wherein the recording medium comprises an elongated magnetic tape.

* * * * *